(12) United States Patent
White et al.

(10) Patent No.: US 10,620,160 B2
(45) Date of Patent: Apr. 14, 2020

(54) METHOD AND APPARATUS FOR ANALYSIS OF GASES

(71) Applicant: Nokia Technologies Oy, Espoo (FI)

(72) Inventors: Richard White, Cambridge (GB); Stefano Borini, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 241 days.

(21) Appl. No.: 15/521,159

(22) PCT Filed: Oct. 15, 2015

(86) PCT No.: PCT/FI2015/050697
§ 371 (c)(1),
(2) Date: Apr. 21, 2017

(87) PCT Pub. No.: WO2016/062918
PCT Pub. Date: Apr. 28, 2016

(65) Prior Publication Data
US 2017/0322181 A1    Nov. 9, 2017

(30) Foreign Application Priority Data
Oct. 24, 2014    (EP) .................................... 14190192

(51) Int. Cl.
*G01N 33/00* (2006.01)
*G01N 27/62* (2006.01)
(Continued)

(52) U.S. Cl.
CPC ....... *G01N 27/622* (2013.01); *G01N 33/0013* (2013.01); *G01N 33/0047* (2013.01);
(Continued)

(58) Field of Classification Search
CPC ...... G01N 27/622; G01N 27/62; G01N 27/00; G01N 33/0013; G01N 33/0047; G01N 1/4005; G01N 2001/4033
(Continued)

(56) References Cited

U.S. PATENT DOCUMENTS 5,877,495 A * 3/1999 Takada ................ H01J 49/0431
250/288
2005/0199799 A1* 9/2005 Takada ................ H01J 49/0095
250/288
(Continued)

FOREIGN PATENT DOCUMENTS

DE    3201989 A1    10/1982
DE    19549144 A1    7/1996
(Continued)

OTHER PUBLICATIONS

International Search Report and Written Opinion received for corresponding Patent Cooperation Treaty Application No. PCT/FI2015/050697 dated Jan. 14, 2016, 15 pages.
(Continued)

*Primary Examiner* — Robert R Raevis
(74) *Attorney, Agent, or Firm* — Harrington & Smith

(57) ABSTRACT

Apparatus comprising an inlet region for receiving a gas mixture; an ionizer for supplying hydronium ions to the received gas mixture to generate ions, wherein the ionizer comprises a membrane for receiving the gas mixture, and wherein the membrane, preferably made of graphene oxide, is capable of generating hydronium ions from water; and an ion detector for detecting ions generated from the gas mixture.

19 Claims, 4 Drawing Sheets

(51) Int. Cl.
*G01N 1/40* (2006.01)
*G01N 33/497* (2006.01)
*B01D 71/02* (2006.01)

(52) U.S. Cl.
CPC .......... *B01D 71/021* (2013.01); *G01N 1/4005* (2013.01); *G01N 2033/4975* (2013.01)

(58) Field of Classification Search
USPC .............. 73/23.2, 23.3, 23.34, 29.01, 29.02, 73/335.02, 29.05, 31.01, 31.02, 31.05, 73/31.07; 422/83, 84, 88, 94, 98
See application file for complete search history.

(56) References Cited

U.S. PATENT DOCUMENTS

| | | | |
|---|---|---|---|
| 2006/0022132 A1* | 2/2006 | Zhang | G01N 27/622 250/290 |
| 2006/0284075 A1 | 12/2006 | Bonne et al. | |
| 2012/0107593 A1 | 5/2012 | Luo et al. | |
| 2014/0207467 A1 | 7/2014 | White et al. | |

FOREIGN PATENT DOCUMENTS

| | | |
|---|---|---|
| DE | 102008026433 A1 | 12/2009 |
| DE | 102011121669 A1 | 6/2013 |

OTHER PUBLICATIONS

Allen, et al., "Simultaneous detection of volatile, semivolatile organic compounds in both air and water matrices by using membrane introduction mass sectrometry", International Journal of Mass Spectrometry, Elsevier Science Publishers, vol. 212, No. 1-3, Nov. 15, 2001, pp. 197-204, XP027401039.

Lagg, et al., "Applications of proton transfer reactions to gas analysis", International Journal of Mass Spectrometry, Elsevier Science Publishers Co., vol. 134, No. 1, Jun. 9, 1994, pp. 55-66 XP026513152.

Extended European Search Report dated Dec. 18, 2014.

* cited by examiner

METHOD AND APPARATUS FOR ANALYSIS OF GASES

RELATED APPLICATION

This application was originally filed as Patent Cooperation Treaty Application No. PCT/FI2015/050697 filed Oct. 15, 2015 which claims priority benefit to EP Patent Application No. 14190192.6, filed Oct. 24, 2014.

TECHNICAL FIELD

The present application relates generally to analysis of gases.

BACKGROUND

Measurement of volatile organic compounds (VOCs) and other trace gases and vapours may be informative, for example, in breath analysis and environmental monitoring. Such breath analysis may be used, for example, for diagnostic purposes.

Methods such as ion mass spectrometry may be used for quantitative measurement of composition of gas and vapour mixtures, and can also be applied to breath analysis or environmental monitoring.

SUMMARY

Various aspects of examples of the invention are set out in the claims.

According to a first aspect there is provided an apparatus comprising an inlet region for receiving a gas mixture; an ionizer for supplying hydronium ions to the received gas mixture to generate ions, wherein the ionizer comprises a membrane for receiving the gas mixture, and wherein the membrane is capable of generating hydronium ions from water; and an ion detector for detecting ions generated from the gas mixture.

According to a second aspect there is provided a method comprising contacting water molecules with a membrane capable of generating hydronium ions from water; contacting a gas mixture with the hydronium ions for generating ions of molecules comprised in the gas mixture; and detecting ions generated.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE EMBODIMENTS

Figure 1:
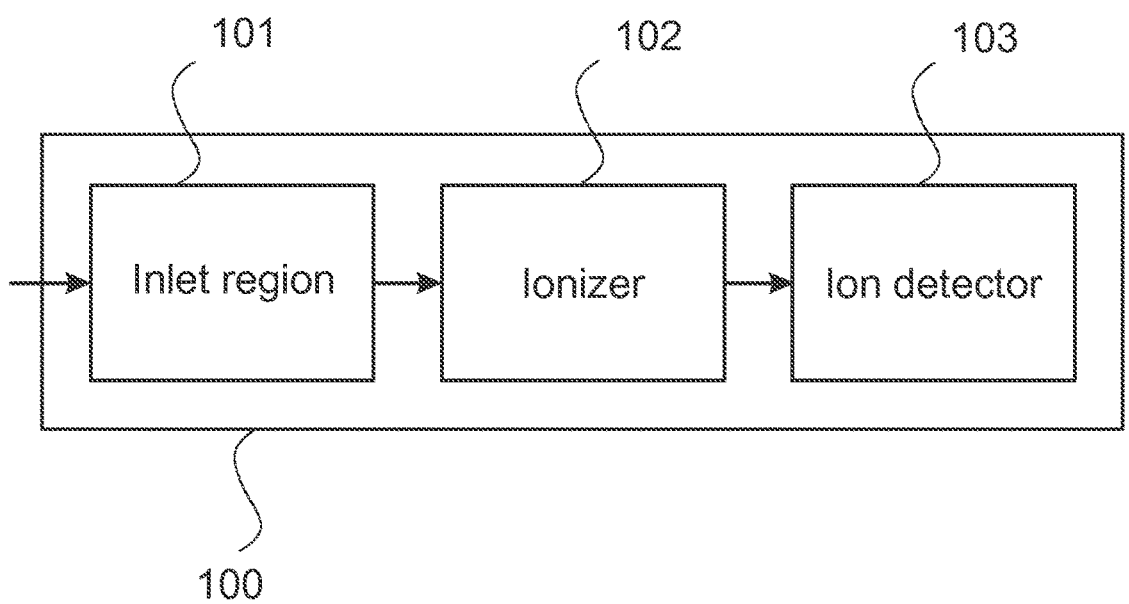
FIG. 1 shows a schematic illustration of an exemplary embodiment of an apparatus.

In an example embodiment, an apparatus comprises an inlet region for receiving a gas mixture; an ionizer for supplying hydronium ions to the received gas mixture to generate ions, wherein the ionizer comprises a membrane for receiving the gas mixture, wherein the membrane is capable of generating hydronium ions from water; and an ion detector for detecting ions generated from the gas mixture.

The inlet region may allow for bringing the gas mixture in contact with the membrane. It may comprise, for example, a tube or a chamber and an inlet orifice. The inlet region may also comprise means for infusing or blowing the gas mixture to the membrane, such as a pump or a syringe.

The term "gas mixture" may refer to molecules of one or more gases and/or vapours, or to a mixture thereof. In an embodiment, the gas mixture comprises molecules of at least one, i.e. one or more, volatile organic compound and water molecules.

The term "hydronium ion" refers to a protonated water molecule, i.e. the ion $H_3O^+$.

The ion detector may, in principle, be any means suitable for detecting or sensing ions. The ion detector may be, for example, an electrometer or a transimpedance amplifier. An electrometer may be capable of measuring at least one of voltage, charge, resistance or current. The ion detector may, for instance, be capable of recording the ion current or the number of ions as a function of time. The ion detector may further comprise, for example, a display or means for recording or analyzing the measurements performed by said means. In an embodiment, the ion detector may be miniaturised.

In an embodiment, an apparatus comprises an inlet region configured to receive a gas mixture; an ionizer configured to supply hydronium ions to the received gas mixture to generate ions, wherein the ionizer comprises a membrane configured to receive the gas mixture, wherein the membrane is capable of generating hydronium ions from water; and an ion detector configured to detect ions generated from the gas mixture.

The ionizer may be an apparatus capable of functioning as an ion source. In an embodiment, the ionizer is a proton-transfer-reaction (PTR) ion source.

The membrane capable of generating hydronium ions from water may, in principle, be any membrane that is capable of generating hydronium ions when in contact with water. When water molecules are contacted with the membrane, hydronium ions may be generated. When molecules of the gas mixture are contacted with the hydronium ions, the hydronium ions are capable of transferring protons to the molecules, and at least some of the molecules may be ionized. Thus the membrane, when provided with water molecules, may be capable of functioning as an ionizer or as means for ionizing molecules comprised in the gas mixture. The term "ionization" may refer to the transfer of protons from hydronium ions to molecules comprised in the gas mixture.

The membrane may be configured to receive molecules of the gas mixture from the input side and to release them from the output side towards the ion detector.

In an embodiment, the membrane is a membrane of a material capable of generating hydronium ions when in contact with water.

In an embodiment, the membrane is a graphene oxide membrane.

Graphene oxide (GO) is a compound comprising carbon, oxygen and hydrogen atoms in variable ratios. Graphene oxide is obtainable by treating graphite with strong oxidizers. Graphite oxide thus obtainable may disperse in basic solutions to yield monolayer sheets of graphene oxide. Graphene oxide membranes may be fabricated, for example, by various solution methods, such as vacuum filtration, spray coating, or spin coating. Graphene oxide is capable of reacting with water molecules to give rise to hydronium ions, i.e. protonated water. The protonation of water by GO may be very efficient, as indicated, for example, by the exponential increase of electrical conductance of GO with increasing relative humidity. Further, many gases such as VOCs may be reactive or very reactive with protons.

In an embodiment, the apparatus comprises a drift region for separating ions according to their ion mobility.

The drift region may also be suitable for filtering ions.

In an embodiment, the drift region comprises at least one of a drift tube or a drift medium. A drift region may comprise at least one drift tube, at least one drift medium, or both. The drift region may also comprise a drift region inlet for receiving ions from the ionizer.

The apparatus or the drift region may comprise means for driving ions towards the ion detector, such as means for generating an electric field, for example, an electrode. The means for generating an electric field may also comprise at least one counter electrode. The drift region may be configured to drive ions towards the ion detector.

In an embodiment, the apparatus comprises an ion detector electrode for driving ions towards the ion detector. The detector electrode may be polarised with respect to the membrane. Such a detector electrode may be configured to generate an electric field within the drift region or drift tube for driving ions from the membrane to the detector electrode. The drift region or drift tube may also comprise one or more distributed electrodes for controlling the electric field distribution along the drift region or drift tube and/or for generating transverse electric fields for filtering ions.

In an embodiment, the drift region or drift tube and detector electrode are miniaturised, for example, by micromachining or microfabrication. For example, they may be fabricated on a Si chip via micromachining and metal deposition.

In an embodiment, the detector electrode is a metal mesh electrode. Such a metal mesh electrode may be configured to allow outlet of gas molecules reaching the electrode.

Ions having a different ion mobility and driven to the drift region simultaneously may reach the ion detector at different time points. The drift region for separating ions according to their ion mobility may comprise means for measuring the time that it takes for ions to migrate through the drift region in the presence of an electric field. This time may be denoted as the drift time. The drift region may be capable of separating ions according to at least one of the following characteristics: size, size/charge ratio, molecular structure, shape, or interactions with a drift medium.

A drift tube may simply be a connection tube, through which ions may drift to the ion detector. The drift tube may also contain therein a drift medium. In an embodiment, the drift medium is a gas. In an embodiment, the drift medium is a buffer gas. A suitable buffer gas may be, for example, nitrogen. The buffer gas may be gas obtainable from the gas mixture, for example, molecules of the gas mixture that are not ionized in the ionizer.

In an embodiment, the drift medium is a membrane capable of generating hydronium ions from water. In an embodiment, the drift medium is a graphene oxide membrane. In an embodiment, the drift region comprises a drift tube, and the drift tube comprises a drift medium, such as a buffer gas.

In an embodiment, the drift region comprises or consists of a membrane capable of generating hydronium ions from water.

In an embodiment, the drift region comprises or consists of a graphene oxide membrane.

In an embodiment, the drift medium is a membrane capable of generating hydronium ions from water. In an embodiment, the drift medium is a graphene oxide membrane.

In an embodiment, the drift medium comprises or consists of a membrane capable of generating hydronium ions from water.

In an embodiment, the drift medium comprises or consists of a graphene oxide membrane.

In such embodiments, the membrane may be configured to separate ions according to their ion mobility through the membrane. Such an embodiment has the technical effect that a separate drift tube may not be necessary, as the graphene oxide membrane, which may be comprised by the ionizer, may be capable and/or sufficient to filter or separate ions according to their ion mobilities. In such embodiments, the apparatus may comprise means for generating an electric field through the membrane. The membrane may have a thickness of e.g. in the range of 1 μm to 1 mm. A thicker membrane may lead to longer drift times through the membrane and subsequently to greater temporal separation of ions.

In the context of this specification, the term "a membrane" may refer to at least one membrane, i.e. one or more membranes. It may also refer to a stack of membranes.

In an embodiment, the membrane is selectively permeable. The microstructure of a graphene oxide membrane, for instance its inter-layer distance, may be adjusted so as to render the membrane selectively permeable to different ions. Thus the membrane may also act as filter or a drift medium for ions.

A graphene oxide membrane may be selectively superpermeable to water. Further, a graphene oxide membrane that is wetted with or immersed in water may be selectively permeable to ions having a certain diameter. For instance, graphene oxide membranes having a thickness of about 5 μm may be selectively permeable to ions having hydrated radii of smaller than 4.5 Å. Further, graphene oxide sheets or membranes may be engineered to exhibit desired gas or ion permeability characteristics. The permeability of the membrane may depend on its porosity. The porosity of a graphene oxide membrane may be increased e.g. by chemical functionalisation.

In an embodiment, the graphene oxide membrane is microporous.

In an embodiment, the apparatus or the drift medium comprises two or more graphene oxide membranes. The ionizer may comprise two or more membranes. The apparatus may also comprise two or more ionizers, wherein each ionizer comprises at least one membrane.

Further, membranes with different permeability may be combined, for example, by stacking. Graphene oxide membranes may be stacked e.g. by contacting a support membrane surface, e.g. polyethersulfone (PES) membrane surface, with the air-liquid interface of a graphene oxide solution and by spin-coating, or by spin-casting a graphene oxide solution on the support membrane surface. In an embodiment, the ionizer comprises a stack of graphene oxide membranes. In an embodiment, the ionizer comprises a stack of two or more graphene oxide membranes. The permeability of each membrane in the stack may be the same or different. In an embodiment, the two or more membranes of the stack have different permeabilities.

In an embodiment, the apparatus comprises an inlet region for receiving a gas mixture; an ionizer for supplying hydronium ions to the received gas mixture to generate ions, wherein the ionizer comprises a graphene oxide membrane or a stack of graphene oxide membranes for receiving the gas mixture and for separating ions according to their ion mobility; and an ion detector for detecting ions generated from the gas mixture.

In an embodiment, the graphene oxide membrane or the surface of the graphene oxide membrane is chemically functionalised. The term "chemical functionalisation" may refer to attachment or introduction of other molecules or species, i.e. molecules or species other than graphene oxide, for instance larger molecules or species, to the graphene oxide. Such other molecules or species may be attached or introduced to GO sheets while in solution. When the GO sheets are deposited, the other molecules or species may be interposed between the GO sheets and may keep the sheets somewhat separated. The chemical functionalisation may thus alter the permeability of the membrane. The graphene oxide membrane may be chemically functionalised covalently or non-covalently. If the graphene oxide membrane is chemically non-covalently functionalised, the functionalisation may be capable of not removing any of the functional groups of the GO itself that are capable of creating protons, i.e. of generating hydronium ions when in contact with water. Suitable other molecules or species for the chemical functionalisation may be e.g. polyethylene glycol (PEG) or $C_{60}$.

In an embodiment, the graphene oxide membrane is formed by a two-stage drying process at or around the triple point of water. For example, a freeze-drying process may be used. Such a graphene oxide membrane may be microporous, and may be permeable to large molecules.

The membrane may also be replaceable and disposable.

The apparatus may also comprise a mass analyzer. A mass analyzer may be an apparatus capable of separating the ions generated according to their mass-to-charge (m/z) ratios. A mass analyzer may also be capable of subsequently recording their number or intensities, or it may be configured to direct ions to the ion detector. Mass analyzers may include, for example, quadrupole mass analyzer, time of flight mass analyzer, magnetic sector mass analyzer, electrostatic sector mass analyzer, quadrupole ion trap mass analyzer, or ion cyclotron resonance mass analyzer.

In an embodiment, the apparatus is a portable apparatus.

In an embodiment, the apparatus is a gas analyzer.

In an embodiment, the apparatus is suitable for detecting volatile organic compounds in a gas and/or vapour phase sample.

In an embodiment, the apparatus is a portable apparatus for detecting volatile organic compounds in a gas and/or vapour phase sample, such as exhaled breath or an environmental sample.

In an embodiment, the apparatus is suitable for analysing a gas mixture. "Gas" and "gas mixture" may also refer to a vapour or a vapour mixture or a mixture of at least one gas and at least one vapour. Vapour (or vapour phase) may be considered to refer to a gas phase at a temperature where the same substance can also exist in the liquid or solid state, below the critical temperature of the substance.

In an embodiment, the gas mixture comprises water molecules. In an embodiment, the gas mixture comprises water molecules and molecules having a higher proton affinity than water.

In an embodiment, the gas mixture is breath.

In an embodiment, the gas mixture is humid air.

In an embodiment, the gas mixture comprises water.

In an embodiment, the water is breath moisture.

In an embodiment, the gas mixture is exhaled breath.

In an embodiment, the gas mixture is an environmental gas sample. Such an environmental sample may be, for example, an air sample or a soil gas sample.

In an embodiment, the ionizer may be configured to supply protons to water molecules comprised in the received gas mixture to generate hydronium ions and to supply the hydronium ions to the received gas mixture.

The proton affinity, $E_{pa}$, of an anion or of a neutral atom or molecule is a measure of its gas-phase basicity. Major gases present in the atmosphere and in breath, such as nitrogen (dinitrogen), oxygen (dioxygen) and carbon dioxide may have a lower proton affinity than water. Therefore trace gases and vapours, such as VOCs, may have a higher propensity to form ions when contacted with hydronium ions. The membrane may thus selectively generate ions of such trace gases and vapours.

Proton affinity of water has, in some experimental measurements, been determined to be 694 kJ/mol at the temperature of 0 K, and 697 kJ/mol at 298 K.

The apparatus may comprise means for modulating flow of generated ions from the ionizer to the drift region and/or ion detector, such as at least one ion shutter. Such means for modulating flow of generated ions may be disposed between the ionizer and the drift region and/or ion detector. Such an ion shutter may comprise, for example, a shutter valve. The means for modulating flow of generated ions to the drift region and/or ion detector, such as an ion shutter, may be configured to provide a pulsed flow of ions into the drift region. The duration of the pulses may be calibrated according to typical values for drift times of the gas or gases, such as VOCs, to be analysed. The means for modulating flow of generated ions, such as an ion shutter, may be miniaturised, for example, by manufacture from a Si chip via micromachining.

In an embodiment, the apparatus comprises an inlet flow modulator. Such an inlet flow modulator may be configured to modulate the flow of the gas mixture into the membrane. It may be disposed between the inlet region and the ionizer.

In an exemplary embodiment, the method comprises contacting water molecules with a membrane capable of generating hydronium ions from water; contacting a gas mixture with the hydronium ions for generating ions of molecules comprised in the gas mixture; and detecting the ions generated.

The term "gas mixture" may refer to molecules of one or more gases and/or vapours, or to a mixture thereof. In an embodiment, the gas mixture comprises molecules of at least one, i.e. one or more, volatile organic compound and water molecules.

In an embodiment, the gas mixture comprises water molecules. In an embodiment, the gas mixture comprises water molecules and molecules having a higher proton affinity than water.

In an embodiment, the method comprises contacting a gas mixture comprising water molecules with a membrane capable of generating hydronium ions from water for generating ions of molecules comprised in the gas mixture; and detecting ions generated.

In an embodiment, the gas mixture is breath.

In an embodiment, the gas mixture is humid air.

In an embodiment, the gas mixture comprises water.

In an embodiment, the water is breath moisture.

In an embodiment, the gas mixture is exhaled breath.

In an embodiment, the gas mixture is an environmental gas sample. Such an environmental sample may be, for example, an air sample or a soil gas sample.

In an embodiment, the method comprises generating ions of molecules comprised in the gas mixture that have a higher proton affinity than water.

In an embodiment, the membrane is a graphene oxide membrane or a membrane of a material capable of generating hydronium ions when in contact with water.

In the context of this specification, the term "a membrane" may refer to at least one membrane, i.e. one or more membranes. It may also refer to a stack of membranes.

In an embodiment, the membrane is selectively permeable. The microstructure of a graphene oxide membrane, for instance its inter-layer distance, may be adjusted so as to render the membrane selectively permeable to different ions. Thus the membrane may also act as filter or a drift medium for ions.

A graphene oxide membrane may be selectively superpermeable to water. Further, a graphene oxide membrane that is wetted with or immersed in water may be selectively permeable to ions having a certain diameter. For instance, graphene oxide membranes having a thickness of about 5 μm may be selectively permeable to ions having hydrated radii of smaller than 4.5 Å. Further, graphene oxide sheets or membranes may be engineered to exhibit desired gas or ion permeability characteristics. The permeability of the membrane may depend on its porosity. The porosity of a graphene oxide membrane may be increased e.g. by chemical functionalisation.

In an embodiment, the graphene oxide membrane is microporous.

In an embodiment, the method comprises separating the ions generated according to their ion mobilities.

In an embodiment, the method comprises separating the ions generated according to their ion mobilities through a membrane capable of generating hydronium ions from water.

In an embodiment, the method comprises separating the ions generated according to their ion mobilities through a graphene oxide membrane.

In an embodiment, the method comprises separating the ions generated according to their ion mobilities through a stack of graphene oxide membranes.

In an embodiment, the method comprises contacting water molecules with a graphene oxide membrane or a stack of graphene oxide membranes for generating hydronium ions from water; contacting a gas mixture with the hydronium ions for generating ions of molecules comprised in the gas mixture; separating the ions generated according to their ion mobilities through a graphene oxide membrane or a stack of graphene oxide membranes; and detecting the ions generated.

The permeability of each membrane in the stack may be the same or different. In an embodiment, the two or more membranes of the stack have different permeabilities.

In an embodiment, the surface of the graphene oxide membrane is chemically functionalised. The term "chemical functionalisation" may refer to attachment or introduction of other molecules or species, for instance larger molecules or species, to the graphene oxide. Such other molecules or species may be attached or introduced to GO sheets while in solution. When the GO sheets are deposited, the other molecules or species may keep the sheets somewhat separated. The chemical functionalisation may thus alter the permeability of the membrane. The graphene oxide membrane may be chemically functionalised covalently or non-covalently. If the graphene oxide membrane is chemically non-covalently functionalised, the functionalisation may not remove any of the functional groups of the GO itself that are capable of creating protons, i.e. of generating hydronium ions when in contact with water. Suitable other molecules or species for the chemical functionalisation may be e.g. polyethylene glycol (PEG) or $C_{60}$.

In an embodiment, the graphene oxide membrane is formed by a two-stage drying process at or around the triple point of water. For example, a freeze-drying process may be used. Such a graphene oxide membrane may be microporous, and may be permeable to large molecules.

An exemplary embodiment involves the use of a membrane capable of generating hydronium ions from water for ionizing molecules of a gas mixture.

An exemplary embodiment involves the use of a membrane capable of generating hydronium ions from water for separating ions of molecules of a gas mixture according to their ion mobility through the membrane.

In an embodiment, the membrane is a graphene oxide membrane or a membrane of a material capable of generating hydronium ions when in contact with water.

In an embodiment, the molecules have a higher proton affinity than water.

In the context of this specification, the term "a membrane" may refer to at least one membrane, i.e. one or more membranes. It may also refer to a stack of membranes.

In an embodiment, the membrane is selectively permeable. The microstructure of a graphene oxide membrane, for instance its inter-layer distance, may be adjusted so as to render the membrane selectively permeable to different ions.

A graphene oxide membrane may be selectively superpermeable to water. Further, a graphene oxide membrane that is wetted with or immersed in water may be selectively permeable to ions having a certain diameter. For instance, graphene oxide membranes having a thickness of about 5 μm may be selectively permeable to ions having hydrated radii of smaller than 4.5 Å. Further, graphene oxide sheets or membranes may be engineered to exhibit desired gas or ion permeability characteristics. The permeability of the membrane may depend on its porosity. The porosity of a graphene oxide membrane may be increased e.g. by chemical functionalisation.

In an embodiment, the graphene oxide membrane is microporous.

The permeability of each membrane in the stack may be the same or different. In an embodiment, the two or more membranes of the stack have different permeabilities.

In an embodiment, the surface of the graphene oxide membrane is chemically functionalised. The term "chemical functionalisation" may refer to attachment or introduction of other molecules or species, for instance larger molecules or species, to the graphene oxide. Such other molecules or species may be attached or introduced to GO sheets while in solution. When the GO sheets are deposited, the other molecules or species may keep the sheets somewhat separated. The chemical functionalisation may thus alter the permeability of the membrane. The graphene oxide membrane may be chemically functionalised covalently or non-covalently. If the graphene oxide membrane is chemically non-covalently functionalised, the functionalisation may not remove any of the functional groups of the GO itself that are capable of creating protons, i.e. of generating hydronium ions when in contact with water. Suitable other molecules or species for the chemical functionalisation may be e.g. polyethylene glycol (PEG) or $C_{60}$.

In an embodiment, the graphene oxide membrane is formed by a two-stage drying process at or around the triple point of water. For example, a freeze-drying process may be used. Such a graphene oxide membrane may be microporous, and may be permeable to large molecules.

In the context of the uses, "gas" and "gas mixture" may also refer to a vapour or a vapour mixture or a mixture of at least one gas and at least one vapour.

In an embodiment, the gas mixture comprises water molecules. In an embodiment, the gas mixture comprises water molecules and molecules having a higher proton affinity than water.

In an embodiment, the gas mixture is breath.

In an embodiment, the gas mixture is humid air.

In an embodiment, the gas mixture comprises water.

In an embodiment, the water is breath moisture.

In an embodiment, the gas mixture is exhaled breath.

In an embodiment, the gas mixture is an environmental gas sample. Such an environmental sample may be, for example, an air sample or a soil gas sample.

An example embodiment of the present invention and its potential advantages are understood by referring to FIGS. 1 through 4 of the drawings.

FIG. 1 shows a schematic illustration of an apparatus. The apparatus 100 comprises an inlet region 101 for receiving a gas mixture. It also comprises an ionizer 102 and an ion detector 103. The flow of the gas mixture to the inlet region 101 and to the ionizer 102 and the flow of ions from the ionizer 102 to the ion detector 103 are depicted with arrows. The apparatus may be suitable for detecting volatile organic compounds in a gas and/or vapour phase sample. In one embodiment, the apparatus is a portable apparatus. The portable apparatus may be used for detecting volatile organic compounds in a gas and/or vapour phase sample, such as exhaled breath or an environmental sample. In another embodiment, the apparatus is a gas analyzer.

Figure 2:
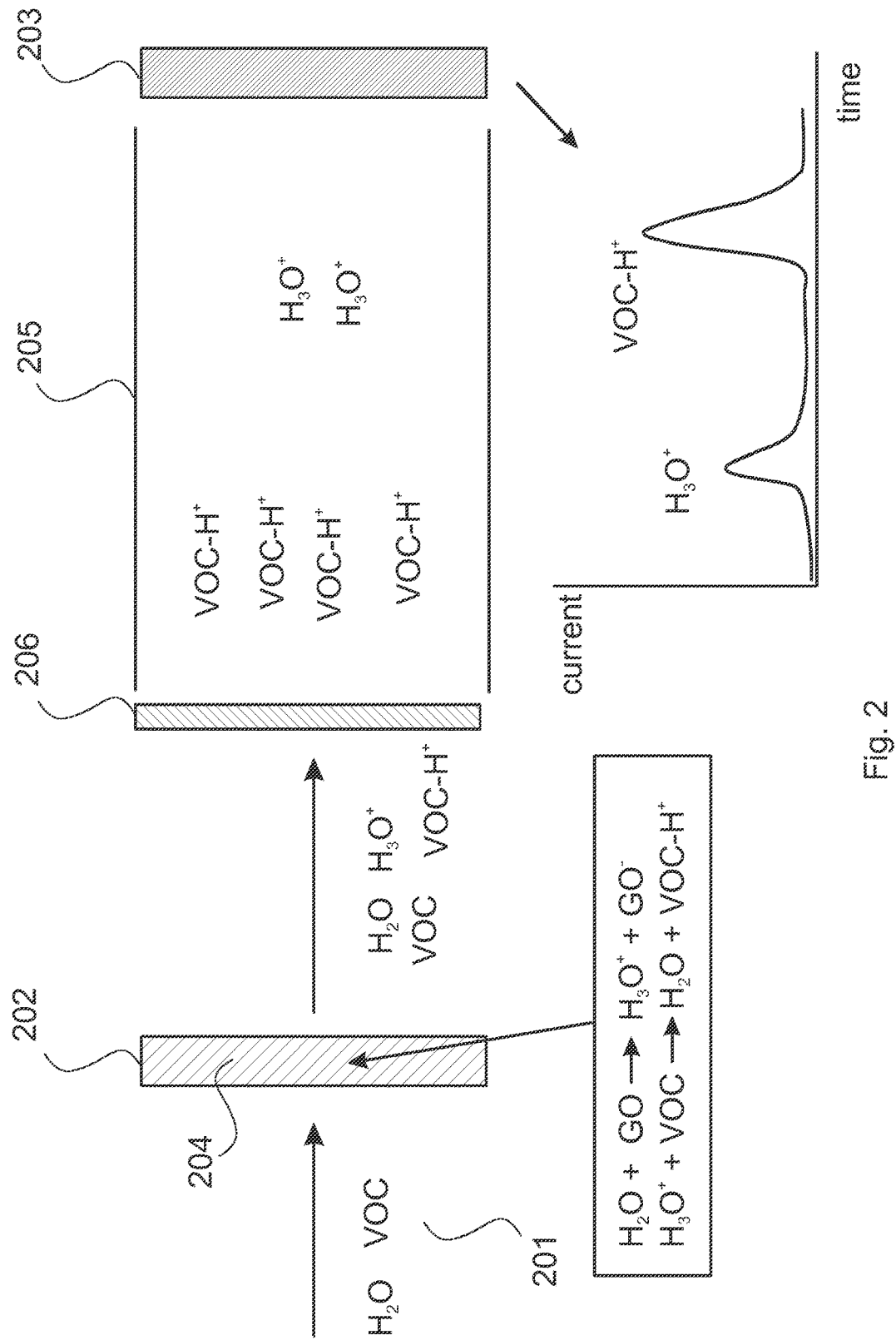
FIG. 2 shows an exemplary embodiment of the present invention.

FIG. 2 shows an exemplary embodiment of the present invention. A gas mixture, such as exhaled breath, denoted in the figure with an arrow, is received in an inlet region 201. The gas mixture comprises molecules of volatile organic compounds, denoted VOC, and water ($H_2O$) molecules. The apparatus comprises an ionizer 202 comprising a membrane 204, for example, a graphene oxide membrane. The molecules contact and pass through the membrane 204. When water molecules are in contact with the membrane 204, at least some of them receive a proton from the graphene oxide (GO) of the membrane, whereby hydronium ions ($H_3O^+$) are generated. The hydronium ions thus generated may then react with molecules of one or more VOCs in order to generated ions of the VOC; protonated VOC is denoted VOC-$H^+$. The hydronium ions and the ions of the VOC then proceed to a drift tube 205. The apparatus further comprises an ion shutter 206, which is configured to modulate the flow of the ions to the drift tube 205. The ions are separated according to their ion mobilities in the drift tube 205. The ions are detected by the ion detector 203, which in this embodiment measures current as a function of time. Ions that may be separated according to their ion mobility in the drift tube 205 may be detected as distinct peaks in the spectrum shown below the schematic of the apparatus.

Figure 3:
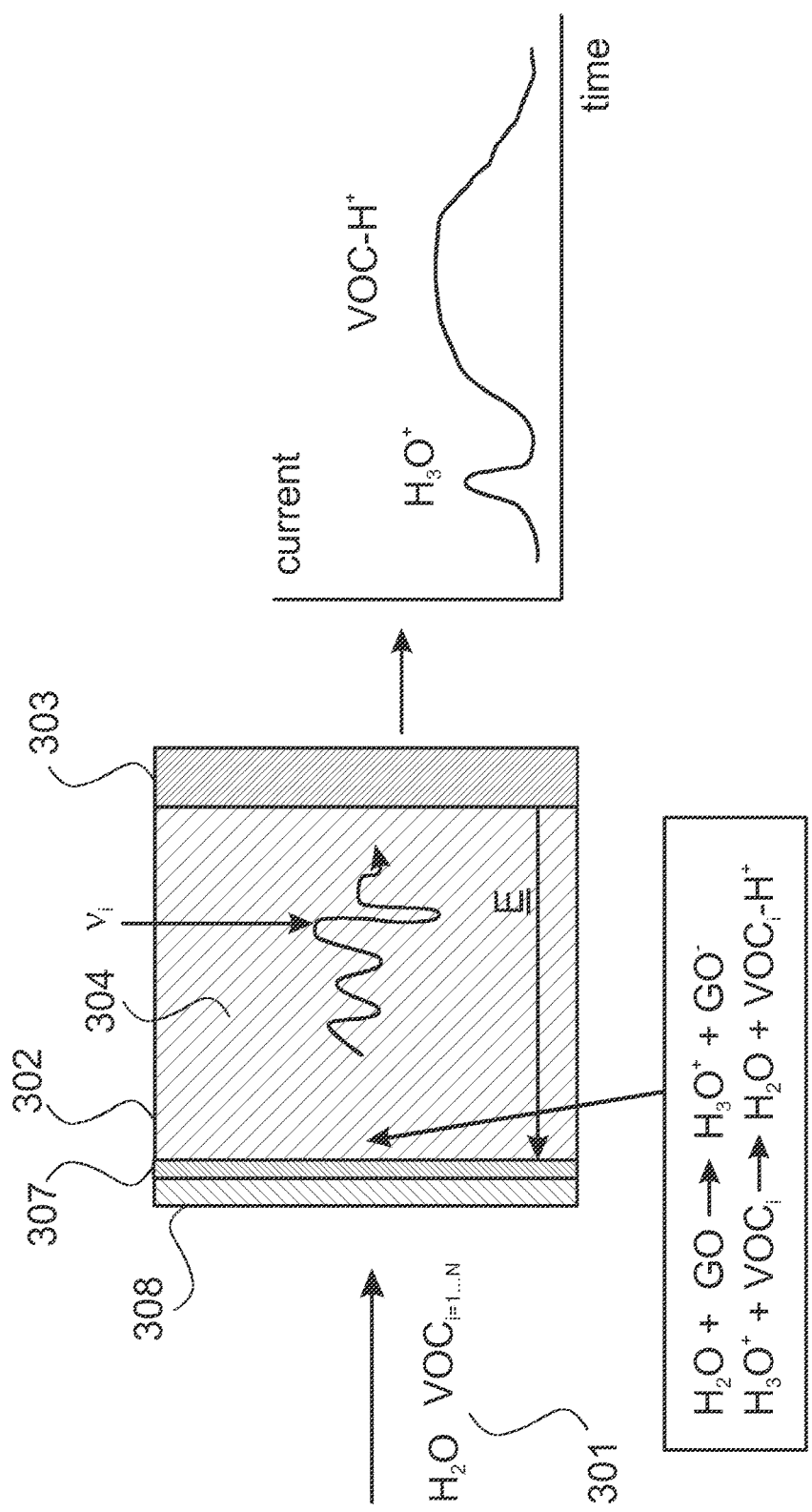
FIG. 3 shows another exemplary embodiment of the present invention.

FIG. 3 shows another exemplary embodiment of the present invention. A gas mixture, such as exhaled breath, denoted in the figure with an arrow, is received in an inlet region 301. The gas mixture comprises molecules of different volatile organic compounds, denoted $VOC_i$, wherein i=1 ... N and N denotes the number of distinct VOC species, and water ($H_2O$) molecules. The apparatus comprises a GO membrane 304 which functions as an ionizer as described above. The apparatus comprises an inlet flow modulator 308, which is configured to modulate the flow of the gas mixture into the membrane 304. The apparatus further comprises a counter electrode 307, which may be configured to form an electric field E through the membrane 304. In this exemplary embodiment, ions may migrate through the membrane 304 towards the ion detector 303 with a velocity $v_i$. Thus the membrane 304 functions as a drift medium. An exemplary path of an ion through the membrane 304 is denoted with the arrow. The ion detector 303 may be in direct contact with the membrane 304. As different ions have different velocities, and subsequently different ion mobilities, they may be detected as peaks in the spectrum shown next to the schematic of the apparatus.

Figure 4:
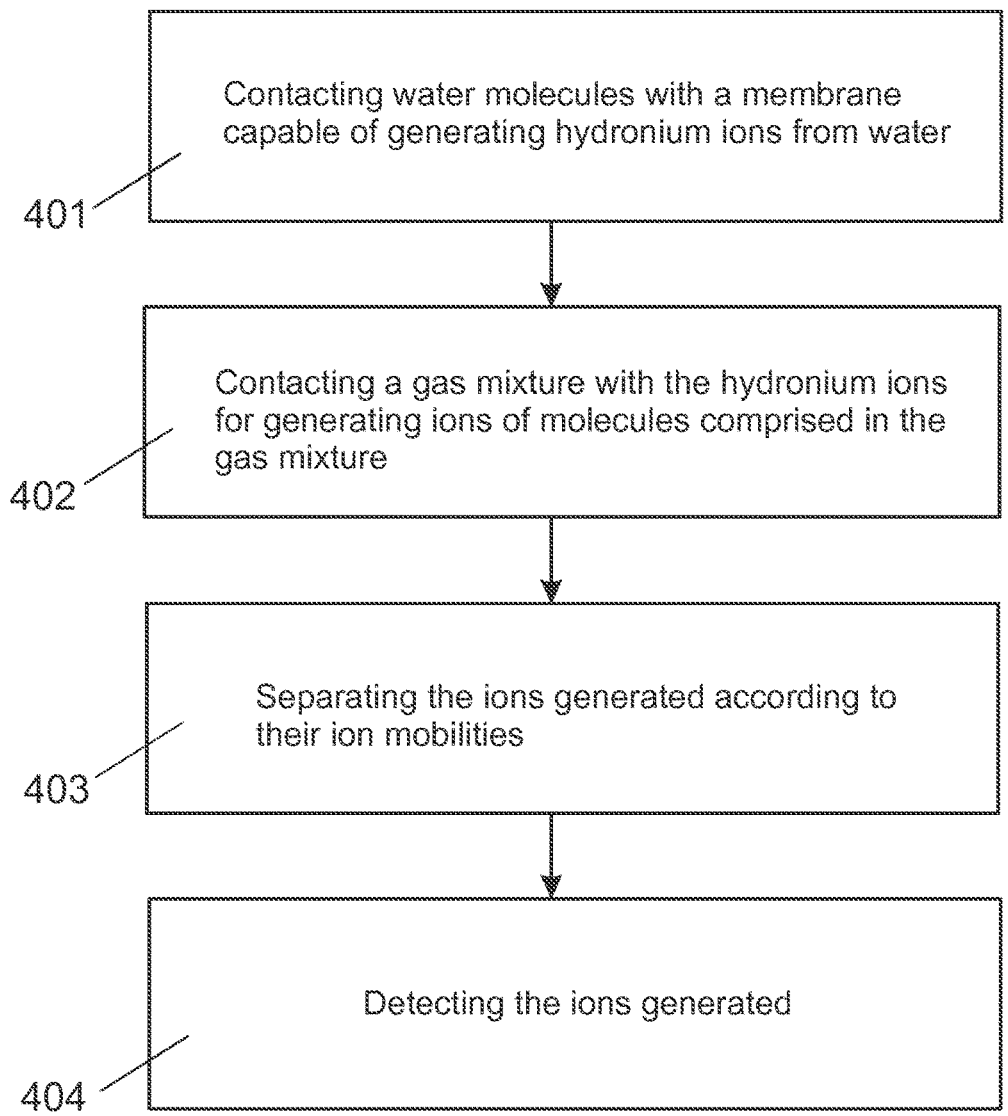
FIG. 4 is flow chart illustration of a method according to an exemplary embodiment.

FIG. 4 is flow chart illustration of a method according to an exemplary embodiment. At 401, water molecules are contacted with a membrane capable of generating hydronium ions from water. At 402, a gas mixture is contacted with the hydronium ions for generating ions of molecules comprised in the gas mixture. Although these are described as consecutive phases in the flow chart, they may also be performed essentially simultaneously. For instance, when the gas mixture, such as exhaled breath, comprises water molecules, both the water molecules and other components of the gas mixture are contacted with the membrane essentially simultaneously; and the hydronium ions generated may react with the molecules comprised in the gas mixture very rapidly within or in the vicinity of the membrane, or after a time period and/or at a distance of the membrane. As hydronium ions transfer protons to the molecules comprised in the gas mixture, ions of the molecules are generated. In this exemplary embodiment, the ions generated may be separated according to their ion mobilities at 403. The separation may be performed using, for example, a suitable drift region. Finally, the ions are detected at 404, for example, using a suitable ion detector.

An apparatus may include at least one processor in communication with a memory or memories. The processor may store, control, add and/or read information from the memory. The memory may comprise one or more computer programs which can be executed by the processor. The processor may also control the functioning of the apparatus. The processor may control other elements of the apparatus by effecting control signaling. The processor may, for example, be embodied as various means including circuitry, at least one processing core, one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application specific integrated circuit (ASIC), or field programmable gate array (FPGA), or some combination thereof.

The memory can include, for example, volatile memory, non-volatile memory, and/or the like. For example, volatile memory may include Random Access Memory (RAM), including dynamic and/or static RAM, on-chip or off-chip cache memory, and/or the like. Non-volatile memory, which may be embedded and/or removable, may include, for example, read-only memory, flash memory, magnetic storage devices, for example, hard disks, floppy disk drives, magnetic tape, etc., optical disc drives and/or media, non-volatile random access memory (NVRAM), and/or the like. If desired, the different functions discussed herein may be performed in a different order and/or concurrently with each other. Furthermore, if desired, one or more of the above-described functions may be optional or may be combined.

Without in any way limiting the scope, interpretation, or application of the claims appearing below, a technical effect of one or more of the example embodiments disclosed herein is that there may not be any need for a separation ionization source or chamber. Another technical effect of one or more of the example embodiments disclosed herein is that the apparatus may be compact or portable. Another technical effect of one or more of the example embodiments disclosed herein is that the apparatus may be of lower cost, for example, to manufacture. Another technical effect of one or more of the example embodiments disclosed herein is that the need for a separate drift region, such as a drift tube, may be eliminated, as the membrane may be capable of functioning as a drift medium.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are several variations and modifications which may be made without departing from the scope of the present invention as defined in the appended claims.

The invention claimed is:

1. An apparatus comprising:
   an inlet region for receiving a gas mixture, the gas mixture including water and at least a second gaseous compound;
   an ionizer for producing hydronium ions from the water in the gas mixture to generate ions, the ionizer including at least one membrane for receiving the gas mixture, and the at least one membrane generating hydronium ions from the water, the ionizer further reacting hydronium ions with the second gaseous compound to produce protonated gaseous compound ions; and
   an ion detector for detecting the hydronium and protonated second gaseous compound ions generated from the gas mixture.

2. The apparatus according to claim 1, wherein the at least one membrane is at least one of a graphene oxide membrane and a membrane of a material capable of generating hydronium ions when in contact with water.

3. The apparatus according to claim 1, further comprising a drift tube for separating ions according to their ion mobility.

4. The apparatus according to claim 3, wherein the at least one membrane is a drift medium.

5. The apparatus according to claim 1, wherein the at least one membrane is selectively permeable.

6. The apparatus according to claim 1, wherein the at least one membrane is a stack of graphene oxide membranes for receiving the gas mixture and for separating ions according to their mobility.

7. The apparatus according to claim 1, wherein the apparatus is a portable apparatus for detecting volatile organic compounds in one of a gas and a vapour phase sample.

8. A method comprising:
   contacting water molecules in a gas mixture including water and at least a second gaseous compound with at least one membrane for generating hydronium ions from water;
   reacting the second gaseous compound in the gas mixture with the hydronium ions to generate protonated second gaseous compound ions; and
   detecting the hydronium and protonated second gaseous compound ions generated.

9. The method according to claim 8, the second gaseous compound has a higher proton affinity than water.

10. The method according to claim 8, wherein the at least one membrane is at least one of a graphene oxide membrane and a membrane of a material capable of generating hydronium ions when in contact with water.

11. The method according to claim 8, wherein the method further comprises separating the ions generated according to their ion mobilities.

12. The method according to claim 8, wherein the method further comprises separating the ions generated according to their ion mobilities through a stack of graphene oxide membranes.

13. The method according to claim 8, wherein the membrane is selectively permeable.

14. A breath analyser comprising:
   an inlet region configured to receive a gas mixture;
   an ionizer comprising at least one membrane configured to generate hydronium ions, the ionizer being configured to use at least the hydronium ions to generate ions from the gas mixture;
   a drift region configured to separate ions according to their ion mobility; and
   an ion detector configured to detect ions generated from the gas mixture.

15. The breath analyser according to claim 14, wherein the at least one membrane is at least one of a graphene oxide membrane and a membrane of a material capable of generating hydronium ions when in contact with water.

16. The breath analyser according to claim 14, wherein the drift region comprises a drift tube.

17. The breath analyser according to claim 14, wherein the at least one membrane is selectively permeable.

18. The breath analyser according to claim 14, wherein the at least one membrane is a stack of graphene oxide membranes.

19. The breath analyser according to claim 14, wherein the at least one membrane is a drift medium.

* * * * *